United States Patent
Liu et al.

(10) Patent No.: US 9,744,145 B1
(45) Date of Patent: Aug. 29, 2017

(54) METHODS FOR TREATING LUNG CANCER

(71) Applicant: Macau University of Science and Technology, Macau (CN)

(72) Inventors: Liang Liu, Macau (CN); Lai-Han Elaine Leung, Macau (CN); Xiao-Jun Yao, Macau (CN); Run-Ze Li, Macau (CN)

(73) Assignee: Macau University of Science and Technology (MO)

( * ) Notice: Subject to any disclaimer, the term of this patent is extended or adjusted under 35 U.S.C. 154(b) by 0 days.

(21) Appl. No.: 15/406,798

(22) Filed: Jan. 16, 2017

(51) Int. Cl.
*A61K 31/18* (2006.01)

(52) U.S. Cl.
CPC .................................... *A61K 31/18* (2013.01)

(58) Field of Classification Search
None
See application file for complete search history.

(56) References Cited

U.S. PATENT DOCUMENTS 8,143,269 B2 * 3/2012 Whitten ............... A61K 31/397
514/290

OTHER PUBLICATIONS

Hannout, et al., J. f. prakt. Chemie. 316:866 (1974).*
American Cancer Society. Cancer Facts and Figures 2015. Atlanta: American Cancer Society; 2015.
Walsh, M.J. et al. ML265, a potent PKM2 activator induces tetramerization and reduces tumor formation and size in a mouse xenograft model; Probe Reports from the NIH Molecular Libraries Program. Bethesda (MD): National Center for Biotechnology Information (US); 2009.
Alfarouk, K.O. et al. Glycolysis, tumor metabolism, cancer growth and dissemination. A new pH-based etiopathogenic perspective and therapeutic approach to an old cancer question. Oncoscience. 2014, 1(12):777-802.
Alfarouk, K.O. et al. Tumor acidity as evolutionary spite. Cancers (Basel). 2011, 3(1):408-414.
Gatenby, R.A. and Gillies, R.J. Why do cancers have high aerobic glycolysis? Nature Reviews Cancer. Nov. 4, 2004 (11):891-899.
Kim, J.W. and Dang, C.V. Cancer's molecular sweet tooth and the Warburg effect. Cancer Res. Sep. 15, 2006 66(18):8927-8930.
Kim, D.J. et al. A Novel Pyruvate Kinase M2 Activator Compound that Suppresses Lung Cancer Cell Viability under Hypoxia. Molecules and Cells. 2015, 38(4):373-379.
Vander Heiden, M.G. et al. Understanding the Warburg effect: the metabolic requirements of cell proliferation. Science. May 22, 2009 324(5930):1029-1033.
Miazurek, S. Pyruvate kinase type M2: A key regulator of the metabolic budget system in tumor cells. The International Journal of Biochemistry & Cell Biology. 2011, 43(7):969-980.
Eigenbrodt, E. et al. Double role for pyruvate kinase type M2 in the regulation of phosphometabolite pools. Cell growth and oncogenesis. 1998, 15-30.
Christofk, H.R. et al. Pyruvate kinase M2 is a phosphotyrosine-binding protein. Nature. 2008, 452(7184):181-186.
Christofk, H.R. et al. The M2 splice isoform of pyruvate kinase is important for cancer metabolism and tumour growth. Nature. 2008,452(7184):230-233.
Spoden, G.A. et al. Isotype-specific inhibitors of the glycolytic keyregulator pyruvate kinase subtype M2 moderately decelerate tumor cell proliferation. International Journal of Cancer. 2008,123(2)312-321.
Boxer, M.B. et al. Evaluation of substituted N,N'-diarylsulfonamides as activators of the tumor cell specific M2 isoform of pyruvate kinase. Journal of Medicinal Chemistry 2010, 53(3):1048-1055.
Anastasiou, D. et al. Pyruvate kinase M2 activators promote tetramer formation and suppress tumorigenesis. Nature Chemical Biology. 2012, (10):839-847.
Parnell, K.M. et al. Pharmacologic activation of PKM2 slows lung tumor xenograft growth. Molecular Cancer Therapeutics. 2013, (8):1453-1460.

* cited by examiner

*Primary Examiner* — Michael Barker
(74) *Attorney, Agent, or Firm* — EAGLE IP LIMITED; Jacqueline C. Lui

(57) ABSTRACT

This invention provides a method of treating lung cancer including administering a therapeutically effective amount of a compound of 0089-0022 formula I to a subject in need thereof. The compound activates pyruvate kinase M2 isoform (PKM2) to treat the lung cancer. In one example, the lung cancer is Non-Small Cell Lung Cancer (NSCLC).

formula I

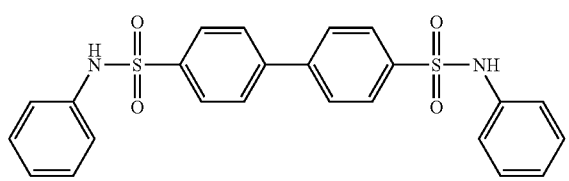

19 Claims, 17 Drawing Sheets
(14 of 17 Drawing Sheet(s) Filed in Color)

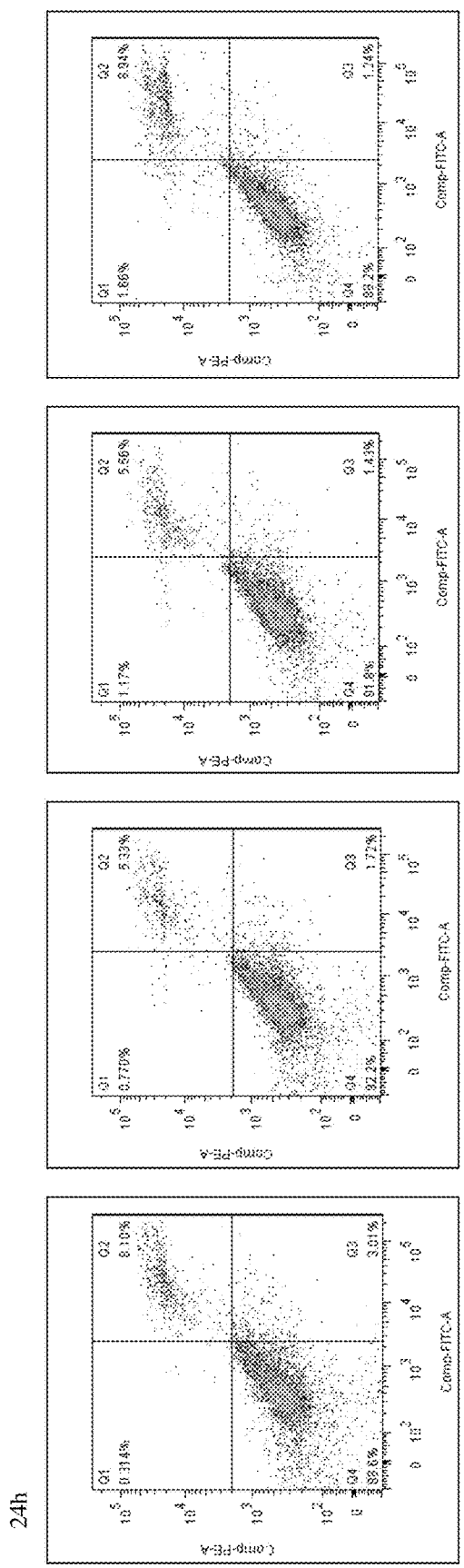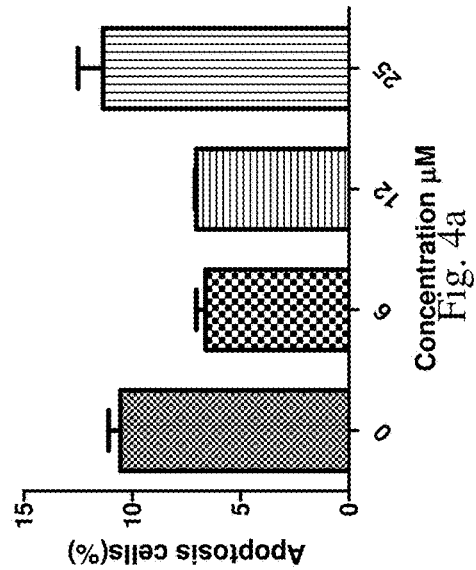
Fig. 4a The effect of Formula (I) on A549

| Cell lines | Primary mutant or derivation | CC50 48h (µM) | CC50 72h (µM) |
|---|---|---|---|
| A549 | EGFR wild type | 20.22 ± 1.85 | 9.33 ± 1.80 |
| H1975 | EGFR L858R + T790M | 10.0 ± 4.12 | 10.63 ± 1.9 |
| HCC827 | EGFR exon 19 deletion | 19.25 ± 1.40 | 15.40 ± 2.76 |
| H820 | EGFR exon 19 deletion + T790M | 57.33 ± 13.24 | 36.69 ± 6.38 |
| H1650 | EGFR exon 19 deletion | 46.13 ± 9.19 | 21.05 ± 2.34 |
| H358 | KRAS | 13.84 ± 2.59 | 13.66 ± 4.44 |
| H460 | Large cell lung cancer cell | 20.15 ± 4.45 | 4.77 ± 2.02 |
| CCD19-LU | Normal lung fibroblast cell | 25.42 ± 6.71 | 15.40 ± 2.76 |
| BEAS2B | Normal lung epithelial cell | 33.76 ± 3.91 | 31.44 ± 3.9 |

Fig. 6

METHODS FOR TREATING LUNG CANCER

BACKGROUND OF INVENTION

Cancer has become the most common death cause disease in China. Carcinoma of the lungs is a leading one among all cancers. Although lots of medicines and therapy methods thereof were invented, the largest obstruction was still the drug resistance.

Cancer cells, different from normal cells, show specific metabolic distinction of the rapid proliferation rate. In 1920's. Otto Warburg observed that cancer cells altered oxidative phosphorylation process into lactic acid fermentation even in aerobic conditions. For rapid proliferating cancer cells, the utilization of extracellular nutrient is 200 times than that of the normal cells.

A different method for the cancer therapy is in need.

SUMMARY OF INVENTION

One example embodiment is a method of treating lung cancer in a patient or a subject, such as a human being, in need thereof. The method includes administering a therapeutically effective amount of a compound to the subject to treat the lung cancer, wherein the compound is presented by formula I

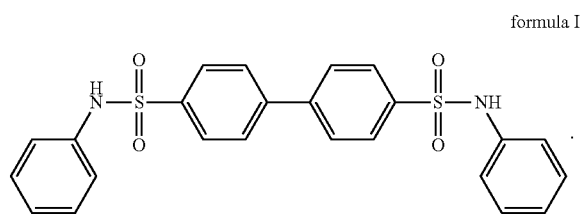 [SMILES: O=S(=O)(Nc1ccccc1)c1ccc(-c2ccc(S(=O)(=O)Nc3ccccc3)cc2)cc1]

formula I

In one example, the lung cancer is Non-Small Cell Lung Cancer. In a further example, the lung cancer is wild type epidermal growth factor receptor (EGFR). In another further example, the lung cancer includes EGFR L858R and T790M mutant.

In one example, the compound activates pyruvate kinase M2 isoform (PKM2) to treat the lung cancer.

In a further example, the method further comprises treating the cancer for 48 hours with a concentration of formula I less than 20.22 µM. In another further example, the method further comprises treating the cancer for 72 hours with a concentration of formula I less than 15.40 µM.

Another example embodiment is a method of treating cancer in a patient or a subject, such as a human being, in need thereof. The method includes administering a therapeutically effective amount of a compound to the patient to treat the cancer, wherein the cancer includes wild type epidermal growth factor receptor (EGFR), or EGFR L858R and T790M mutant, and the compound is presented by formula I

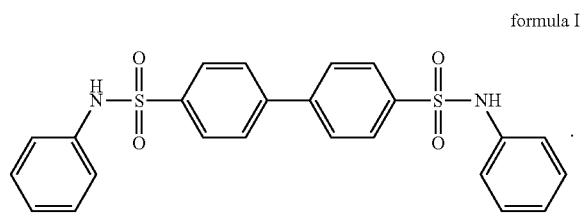

formula I

In one example, the compound activates pyruvate kinase M2 isoform (PKM2) to treat the cancer.

In another example, the cancer is lung cancer. In a further example, the cancer is Non-Small Cell Lung Cancer (NSCLC).

In another example, the method further comprises treating the cancer for 48 hours with a concentration of formula I less than 20.22 µM. In another example, the method further comprises treating the cancer for 72 hours with a concentration of formula I less than 15.40 µM.

Another example embodiment is a method of treating cancer in a patient or a subject, such as a human being, in need thereof. The method includes diagnosing the subject having cancers including wild type epidermal growth factor receptor (EGFR), or EGFR L858R and T790M mutant; administering a therapeutically effective amount of a compound to the patient to treat the cancer, and the compound is presented by formula I

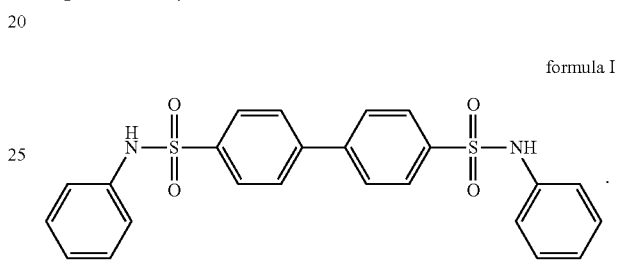

formula I

In one example, the compound activates pyruvate kinase M2 isoform (PKM2) to treat the cancer.

In another example, the cancer is lung cancer. In a further example, the cancer is Non-Small Cell Lung Cancer (NSCLC).

In another example, the method further comprises treating the cancer for 48 hours with a concentration of formula I less than 20.22 µM. In another example, the method further comprises treating the cancer for 72 hours with a concentration of formula I less than 15.40 µM.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 4a, FIG. 4b, FIG. 4c, FIG. 4d, FIG. 4e and FIG. 4f show the flow cytometric analysis of apoptosis level after PKM2 activator formula I treatment for 24 hours, 48 hours and 72 hours in A549 and H1975 cell lines respectively.

FIG. 6 shows the cellular viability profiles for PKM2 activator formula I.

DETAILED DESCRIPTION OF THE PREFERRED EMBODIMENTS

Figure 1A:
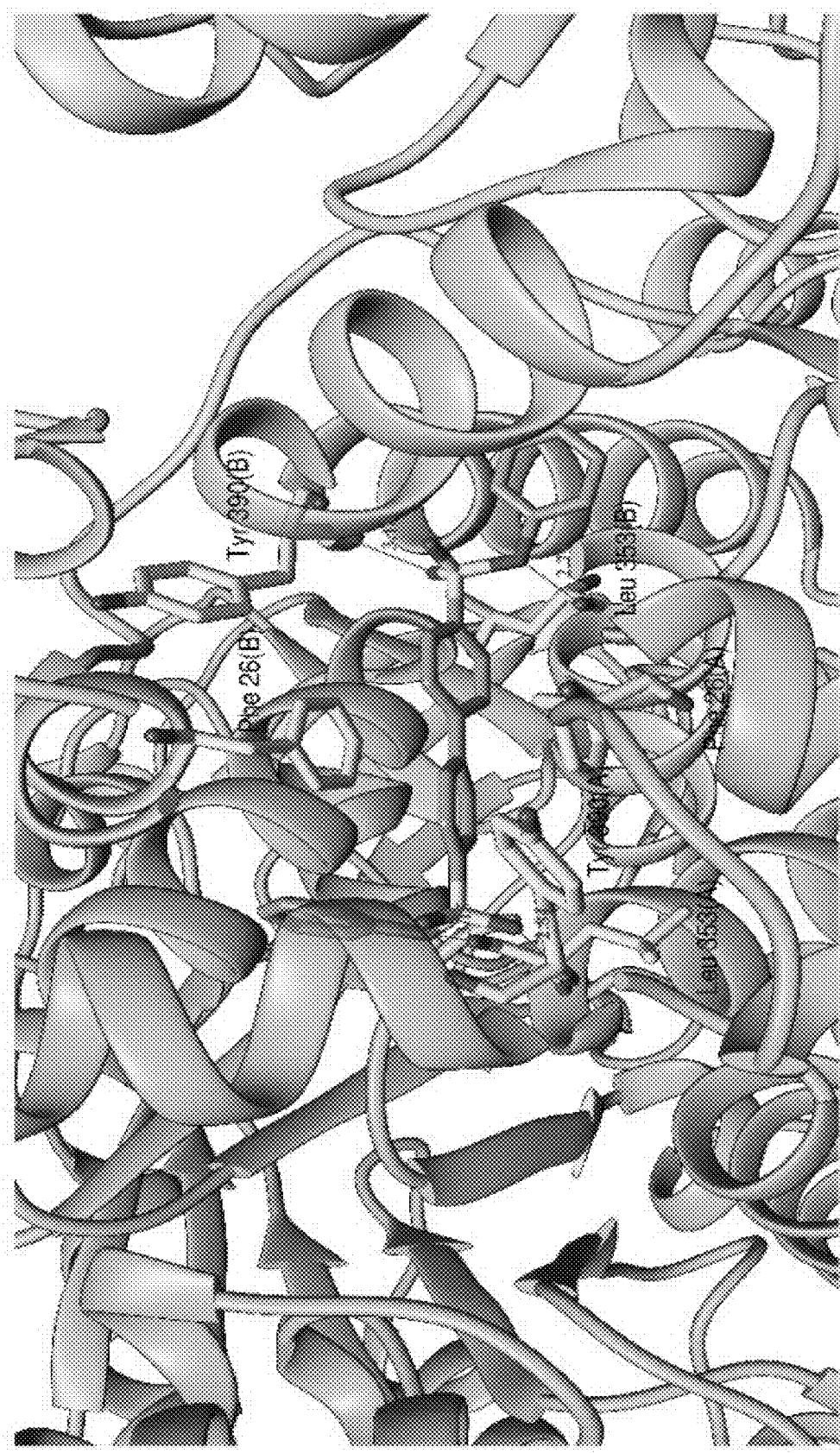
FIG. 1a shows the binding mode of formula I to dimeric PKM2. The chain A and chain B were colored green and cyan respectively. Formula I was colored orange and the residues in the binding site was colored yellow. The hydrogen bonds were shown in red solid and the corresponding distances were labelled.

As used herein and in the claims, "comprising" means including the following elements but not excluding others.

Pyruvate kinase M2 isoform (PKM2), a key mediator of glycolysis, is a rate limiting enzyme, which catalyzes the final step in glycolysis, transfers the phosphate from phosphoenolpyruvate (PEP) to adenosine diphosphate (ADP). In mammals, there are totally four isoforms of pyruvate kinase, PKL, PKR, PKM1 and PKM2, encoded by two genes, Pkrl and Pkm. PKL is mainly expressed in liver meantime; PKR is in red blood cells; both of which are encoded by Pkrl. PKM1 is found in many normal tissues, but PKM2 is expressed in highly proliferating cells; both of which are encoded by Pkm. PKM2 has a special characteristic that it can alter into two function forms: the active tetrameric form and the inactive dimeric form. The tetrameric PKM2 has a high affinity for PEP and leads glycolysis by the pyruvate oxidation in mitochondria. Dimeric PKM2 has a low affinity for PEP and leads glycolysis by lactic acid fermentation in the cytosol. Cancer cells prefer the dimeric PKM2 to increase the glucose uptake, and this action facilitates accumulation of the glycolytic intermediates for the anabolic processes, like the syntheses of nucleic acid, amino acid and lipid.

If using RNA interference to knock down PKM2, cancer cells' growth was significantly inhibited. Further, if PKM2 were switched to the pyruvate kinase M1 isoform, the tumor formation and growth were slowed down in vivo. Thus, the metabolic differences provide a potential for a treatment of cancers.

PKM2 activators aim to induce tetramerization of PKM2. The first small molecules to activate PKM2 was reported by the NIH chemical genomics center. After that, more activators have been reported, but only a few were tested in vitro and in vivo.

In an example embodiment in accordance with the invention, a new PKM2 activators was screened out using molecular docking screening technique. Kinase-based and cell-based assays were utilized to detect the PKM2 activation of several compounds on two NSCLC cell lines (A549 and H1975, which are EGFR wild type and EGFR double mutant (T790M/L858R) respectively). The result showed that formula I was a potent PKM2 activator. It can directly activate PKM2 activity through phosphorylation of PKM2, further induce apoptosis in A549 and H1975 cell lines via regulation of glycolysis. This compound can be developed as a new anti-cancer drug for lung cancer.

Material and Methods

1. Cell Culture and Reagents

Seven lung cancer cell lines (A549, H1975, HCC827, H820, H1650, H358 and H460) and two normal cell lines (CCD19-LU and BEAS2B) were purchased from ATCC (American type culture collection). The lung cancer cell lines were cultivated with RPMI 1640 medium. CCD19-LU were cultivated with MEM medium supplement with 10% fetal bovine serum. Both 1640 medium and MEM medium were supplemented with 10% fetal bovine serum (FBS) and 100 U/mL penicillin and 100 μg/mL streptomycin (Gibco, Big Cabin, Okla., ME, USA) (Gibco, Big Cabin, Okla., ME, USA), 100 U/mL, penicillin and 100 μg/mL and streptomycin (Gibco, Big Cabin, Okla., ME, USA). BEAS2B were cultivated in culture flasks pre-coated with a mixture of 0.01 mg/ml fibronectin, 0.03 mg/ml bovine collagen type I and 0.01 mg/ml bovine serum albumin dissolved in BEBM medium (Lonza, Allendale, N.J., US). The cells were cultured in incubator with 5% CO2 at 37° C.

Formula I was purchased from Top Science Co. Ltd (Shanghai, China). primary anti-bodies of β-actin, total/phosphor-PKM2(T-/P-PKM2), total/phosphor-AKT (T-IP-AKT), BCL-2 were purchased from Cell Signaling Technology (Danvers Mass., USA). Fluorescein-conjugated anti-rabbit as secondary anti-body was purchased from Odyssey (Belfast, Me., USA).

2. MTT Cytotoxicity Assay

Cells were seeded in a 96-well microplate with 3000-5000 cells/well confluence, and put into an incubator overnight for cells adhesion. Different concentrations of formula I were added with DMSO as vehicle control. The microplates were incubated for another 48 hours and 72 hours separately. Each dosage was repeated in triplicate. 10 μL of MTT (5 mg/mL) solution was added to each well. The plate was then placed back into the incubator for 4 hours. After that, 100 μL of resolved solution (10% SDS and 0.1 mM HCL) was added to each well. Before dissolving the formazan crystals, the microplate was put back into the incubator for another 4 hours. The absorbance of the plate was measured at 570 nm with reference 650 nm by a microplate reader (Tecan, Morrisville, N.C., USA). Cell viability was calculated by percentages of the absorbance of the treatment group divided by the absorbance of untreated group. At least three independent experiments were performed for data analysis and presentation.

3. Apoptosis Assay

A549 and H1975 cells ($1 \times 10^5$ cells/well) were seeded in a well plate with 6 wells for 24 hours, and treated with the indicated concentrations of formula I for an additional 24 hours, 48 hours and 72 hours at 37° C. After indicated hours, the cells were washed by ice-cold 1×PBS once and harvested by trypsination. Then cells were centrifuged, collected, and resuspended in ice-cold 1×PBS. After removing the supernatants, cell pellets were re-suspended in 100 μL 1×Annexin-binding buffer. The cells were then double-stained with Annexin-V FITC and PI (100 μg/mL) of 2 μL respectively for 15 min at room temperature in dark. After that, 300 μL 1× Annexin-binding buffer was added. Apoptotic cells were quantitatively counted by a BD Aria III Flow Cytometer (BD Biosciences, San Jose, Calif., USA)

4. Western Blot Analysis

After incubation A549 and H1975 cells with formula I for 24 hours and 72 hours, A549 and H1975 cells were harvested and washed with cold 1×PBS. Then, cells were lysed with ice-cold RIPA lysis buffer with protease, and phosphatase inhibitors were added to extract the cell protein extraction. The supernatants were collected by centrifugation at 12,000 g, for 5 minutes. The quantitation of total protein extraction was measured by Bio-Rad DCTM protein assay kit (Bio-Rad, Philadelphia, Pa., USA). Then 30 μg of protein were loaded and electrophoretically separated on 8% SDS-PAGE gel and then transferred to Nitrocellulose (NC) membrane. Membranes were blocked with 5% non-fat milk and PBS containing 0.1% Tween-20 (TBST) for 1 hour at room temperature. After 1 hour, membranes were incubated with primary anti-bodies (1:1000 dilution) against β-actin, total/phosphor-PKM2, total/phosphor-AKT, and BCL-2 at 4° C. with gently shaking overnight. Membranes were washed with TBST for 3 times (5 minutes/time), and incubated with secondary fluorescent antibody (1:10000 dilutions) for 1 hour at room temperature. Rewashing with TBST for 3 times (15 minutes/time), the stripes were visualized by LI-COR Odessy scanner (Belfast, Me., USA).

5. PKM2 Enzyme Activity Assay

PKM2 biochemical assay Compounds were pre-incubated with 2 nmol/L PKM2 enzyme in reaction buffer (50 mmol/L Tris-HCl, pH 8.0, 200 mmol/L KCl, 30 mmol/L MgCl2, 2 mmol/L dithiothreitol (DTT), 5% DMSO) for 30 minutes at room temperature. ADP and PEP were then added to final concentrations of 75 mmol/L and 15 mmol/L, respectively. After 30 minutes, ATP formation was measured by KINASE GLO® Plus from Promega, and Concentration at half-maximal activation (AC50) values were determined using Prism GraphPad Software.

6. Molecular Docking Study on the Interaction Between Formula I and PKM2.

Molecular docking calculation is performed to study the interaction between formula I and the homodimer interface of PKM2 by Induced Fit Docking module in Schrodinger software (Schrodinger, Inc., New York, N.Y., 2009). The studied compound is prepared and optimized in the LigPrep module. The 3D structure of PKM2 is derived from the PDB database (PDB ID: 3ME3) and prepared using the Protein Preparation Wizard. During the induced fit docking, centroid of the co-crystalized ligand is defined as the active site and the pose of ligand is valued with XP docking score. The pose with the highest score is selected for further analysis.

7. Statistical Analysis

All the data were presented as mean±SD of 3 individual experiments. Differences were analyzed by one-way ANOVA using Graph Prism 5.

Results

1. Molecular docking showed that formula I is a direct PKM2 activator by binding to the kinase pocket.

Figure 1B:
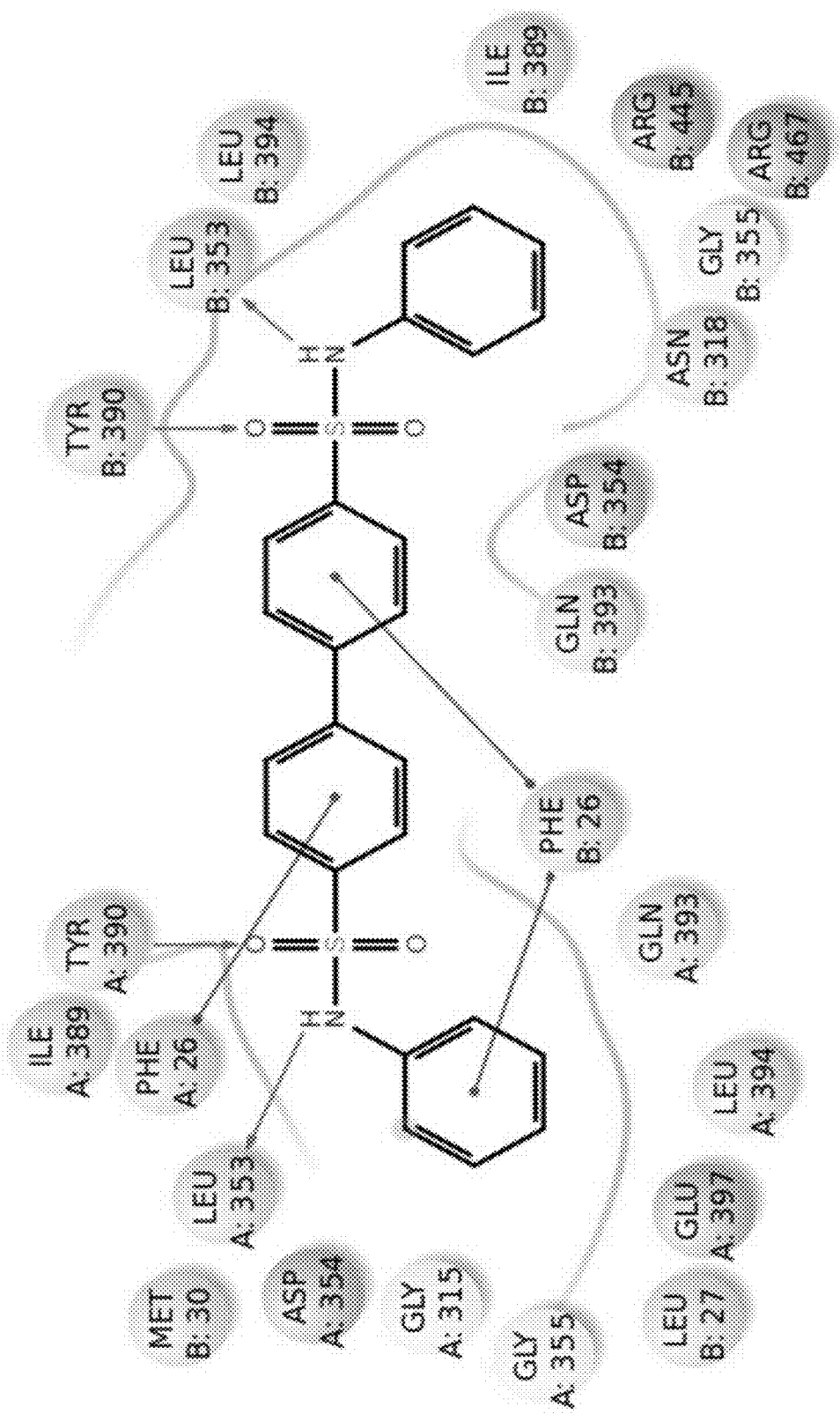
FIG. 1b shows the 2D representation of the interaction between formula I and dimeric PKM2. The hydrogen bonding and π-π stacking were colored in purple and green.

The binding affinity of formula I was evaluated by the XP docking score. The best pose with a docking score of −12.038 Kcal/mol was selected to represent the acceptor-ligand binding modes. As shown in FIG. 1a and FIG. 1b, the interaction between formula I and the homodimer of PKM2 occurred symmetrically. According to FIG. 1a, the oxygen atom and nitrogen atom in each sulfonyl group of formula I formed hydrogen bonding interactions to the corresponding backbone atoms of Leu353 and Tyr390 in both chains. The biphenyl group of formula I was settled in the middle of two Phe26 and formed a close π-π stacking interaction with both Phe26 in the dimer. The residues around the binding site shown in FIG. 1b was colored according to their hydrophobicity. It was observed that the binding site was mainly constituted by a series of hydrophobic and aromatic residues (colored in green). So the hydrophobic interaction between the acceptor and ligand seemed to be the vital factor for ligand affinity.

2. Enzyme Activity Assay Showed that Formula I Had the PKM2 Activating Ability.

Figure 2:
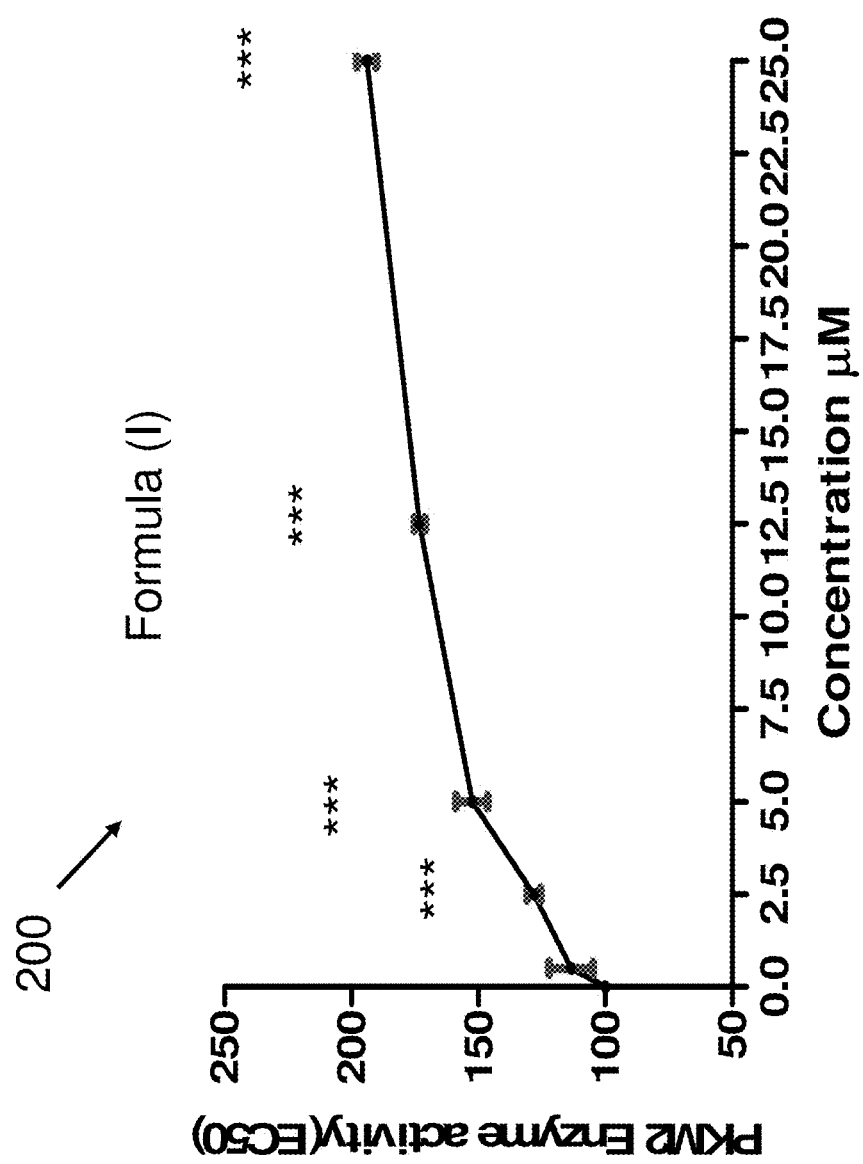
FIG. 2 shows a graph of the PKM2 enzyme activity over the concentration of formula I.
Figure 3B:
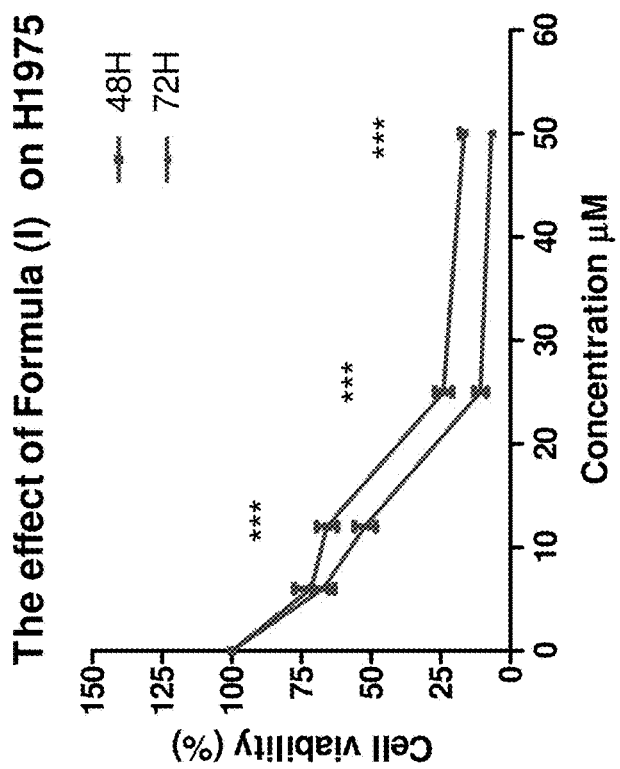
FIG. 3a, FIG. 3b, FIG. 3c, FIG. 3d, FIG. 3e, FIG. 3f, FIG. 3g, FIG. 3h and FIG. 3i show graphs of viability effects induced by PKM2 activator formula I in different lung cancer cell lines (A549, H1975, HCC827, H820, H1650, H358 and H460), normal lung fibroblast cell line CCD19-LU and normal lung epithelial cell line BEAS2B respectively at two time points.
Figure 3A:
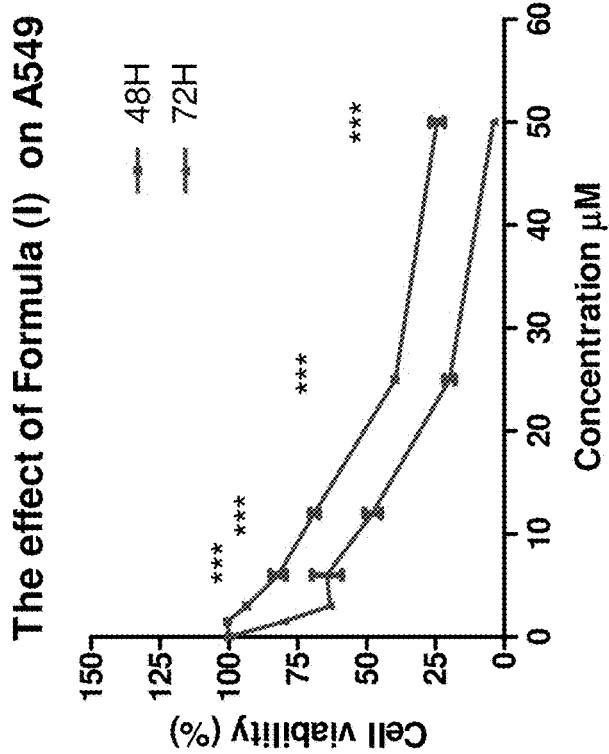
Figure 3D:
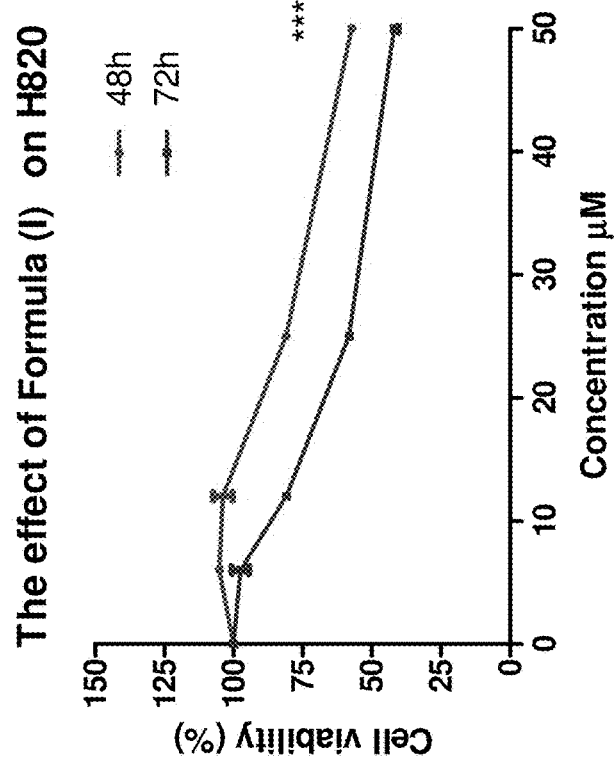
Figure 3C:
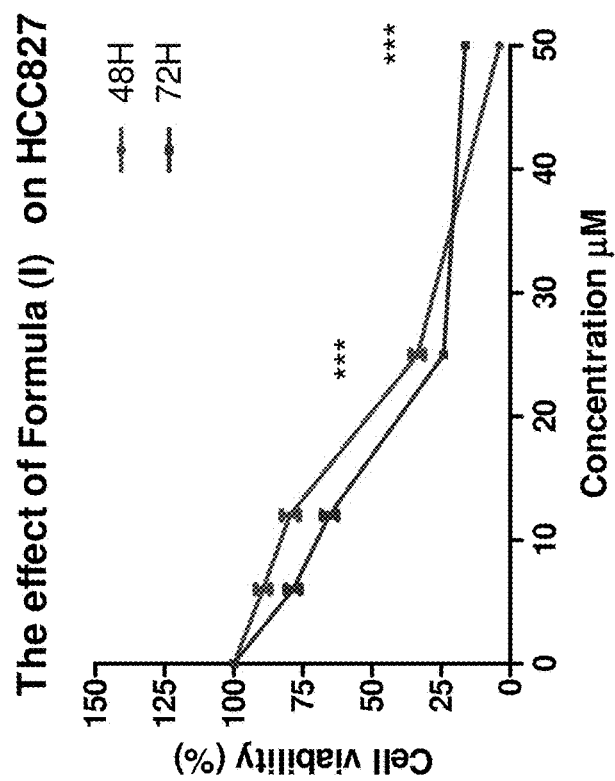
Figure 3F:
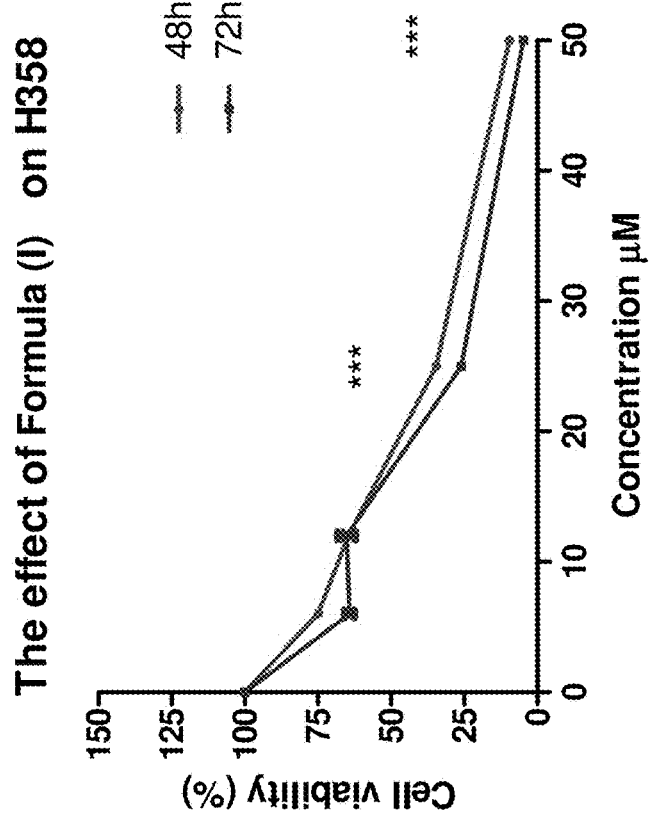
Figure 3E:
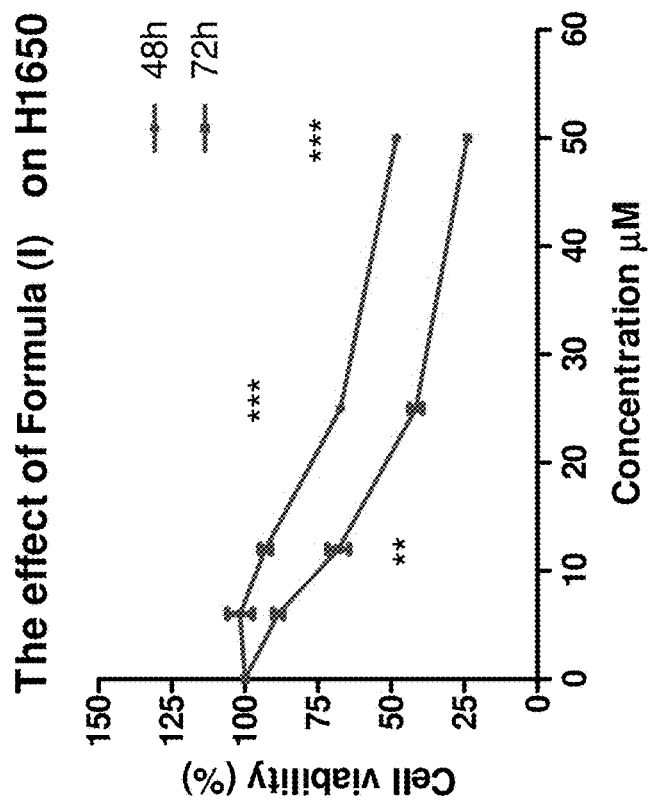
Figure 3G:
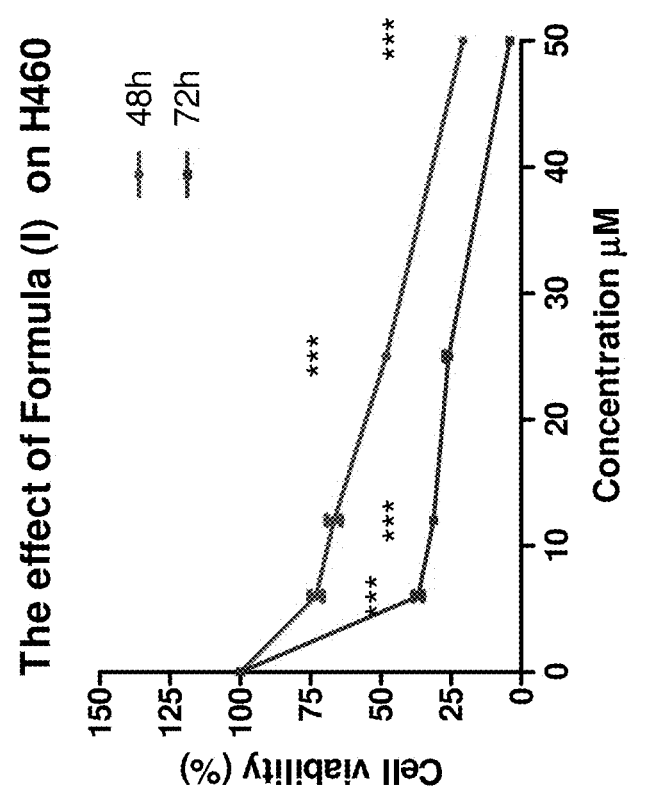
Figure 3I:
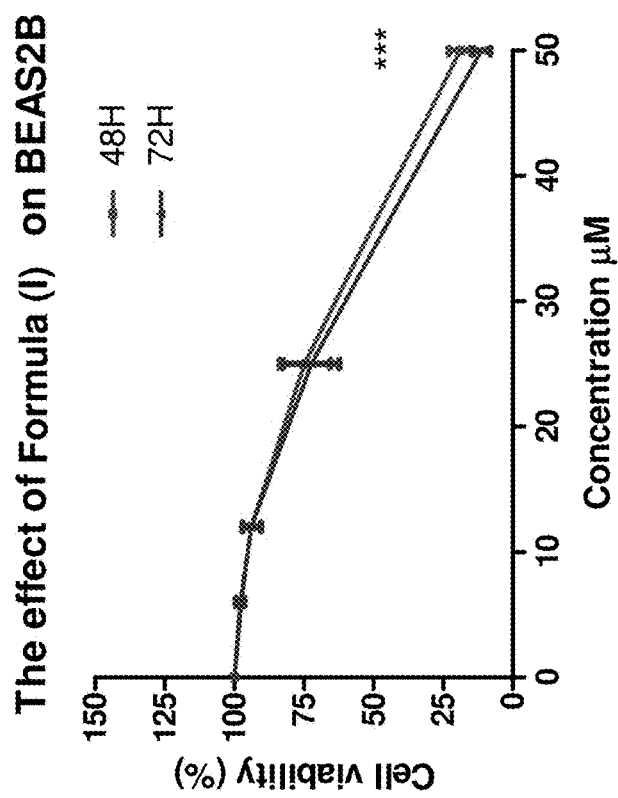
Figure 3H:
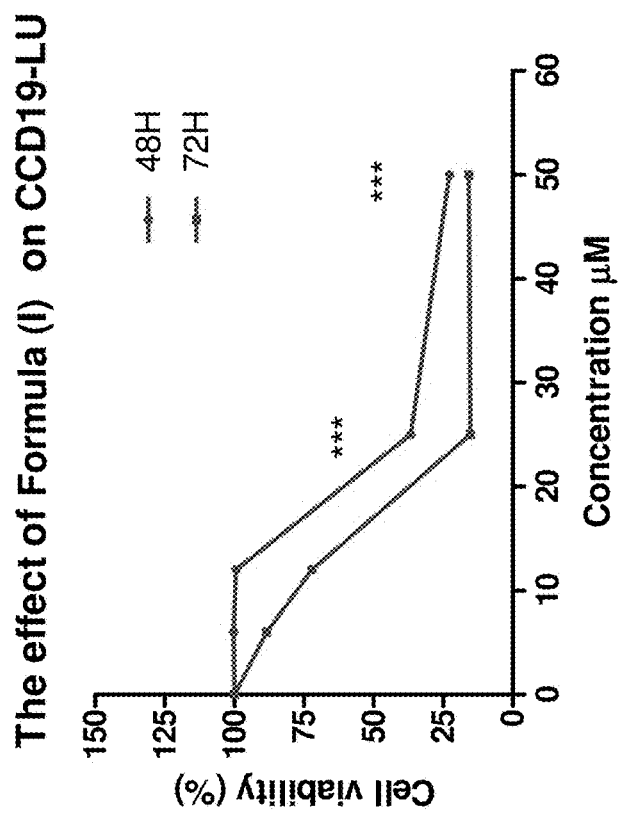
Figure 4B:
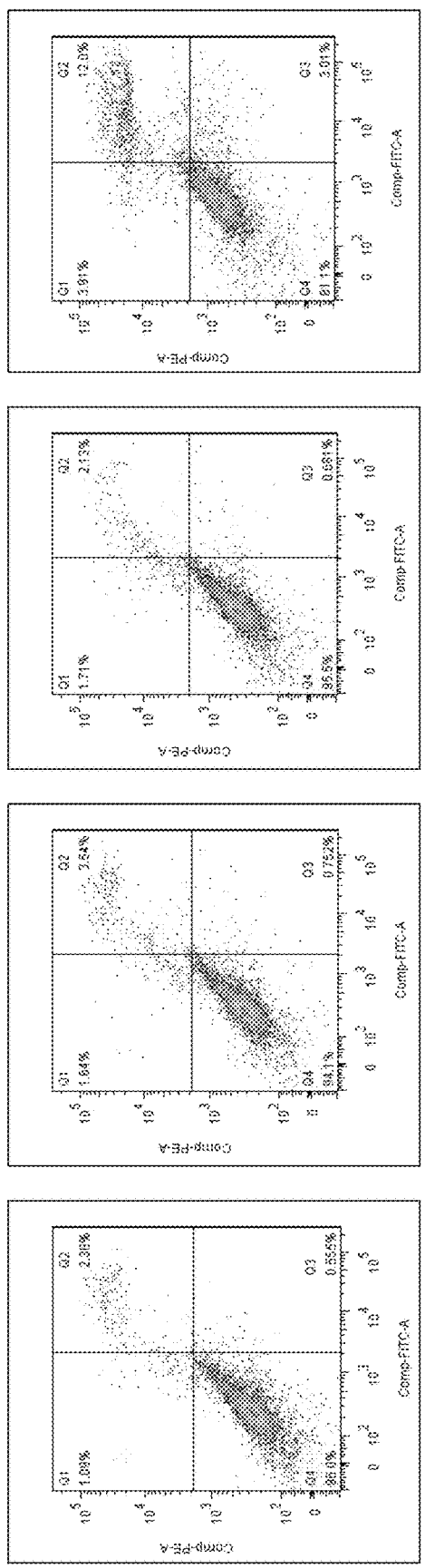
Figure 4B:
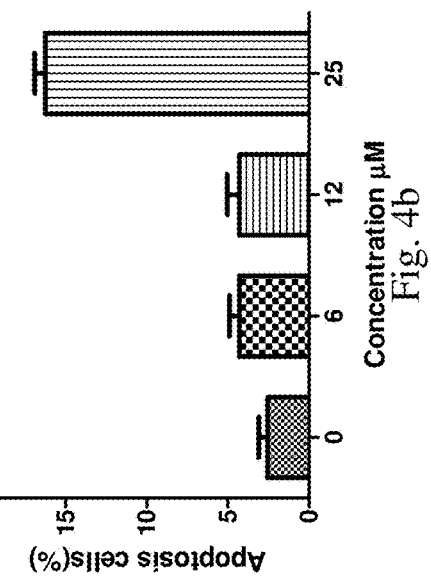
Figure 4C:
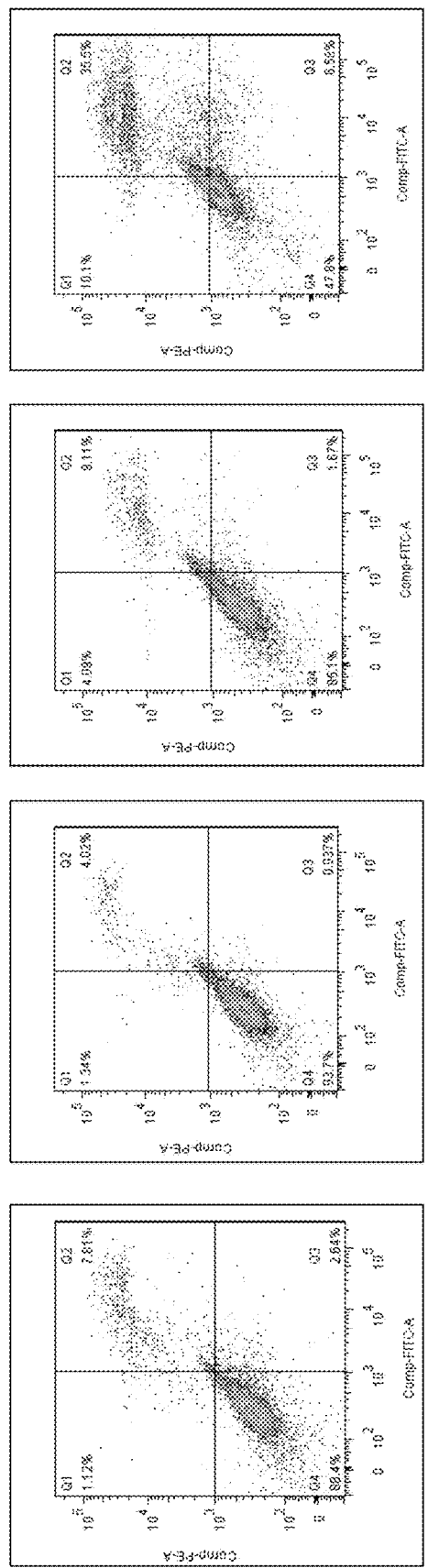
Figure 4C:
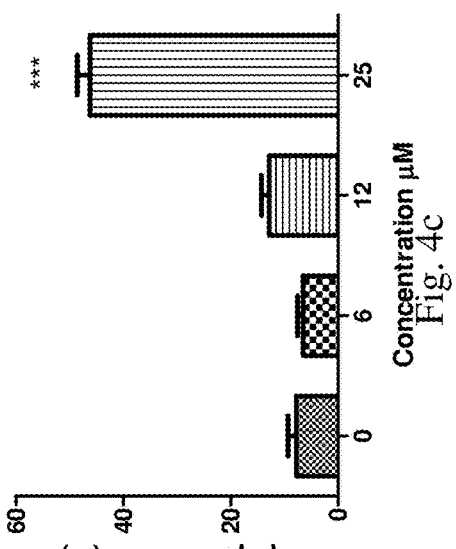
Figure 4D:
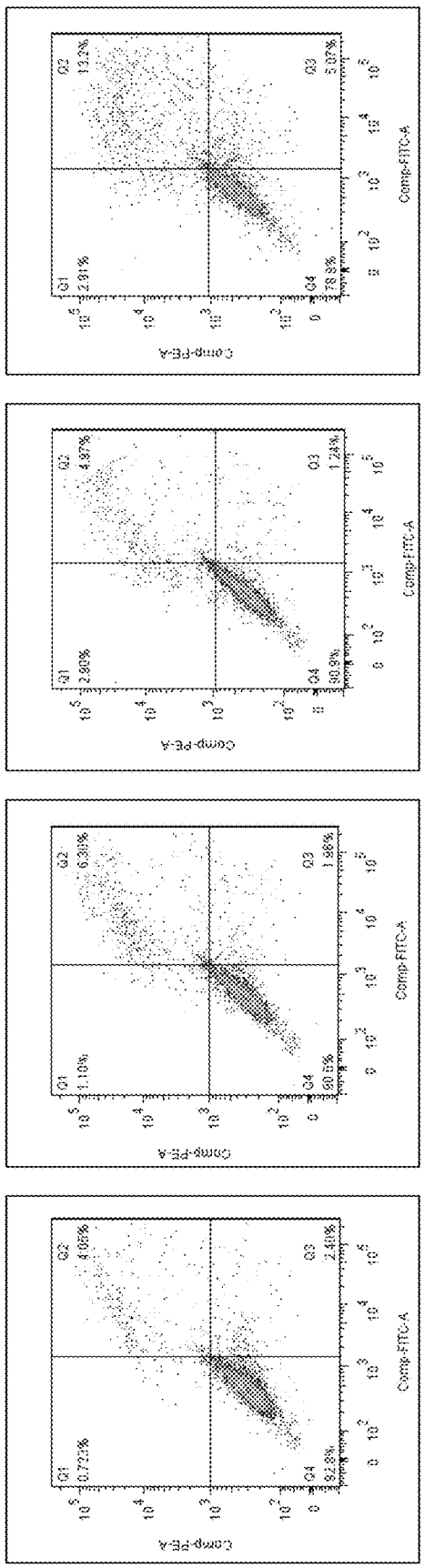
Figure 4D:
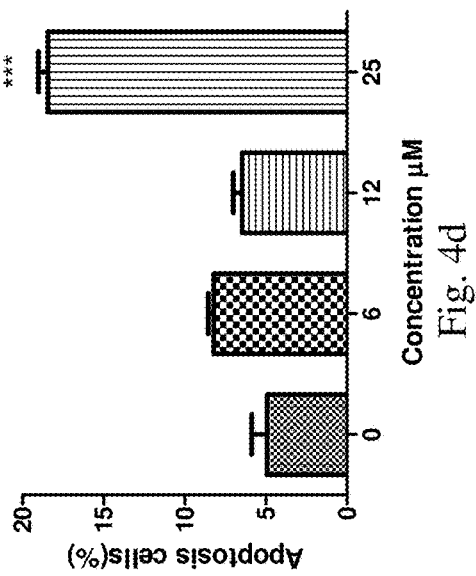
Figure 4E:
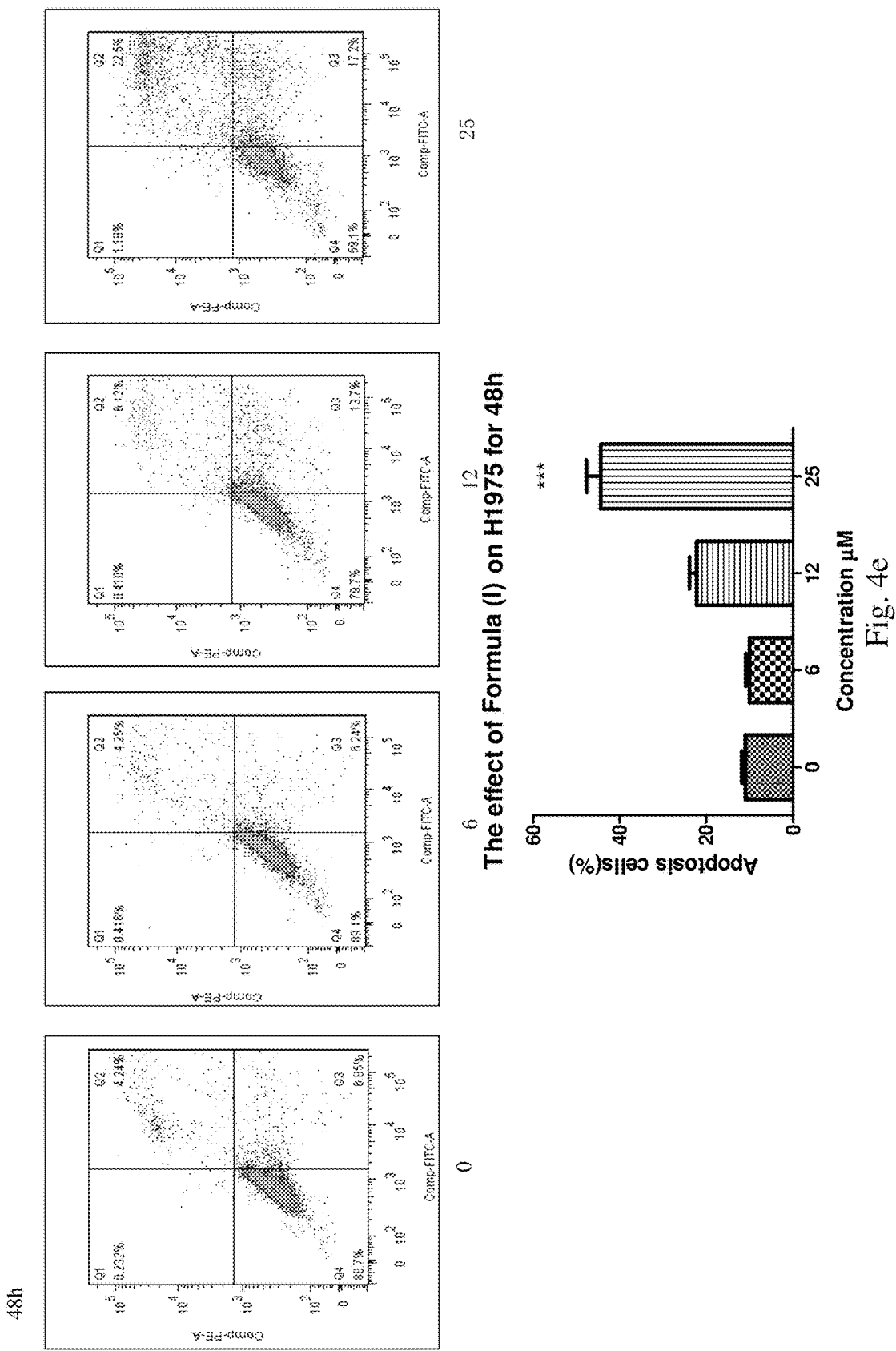
Figure 4F:
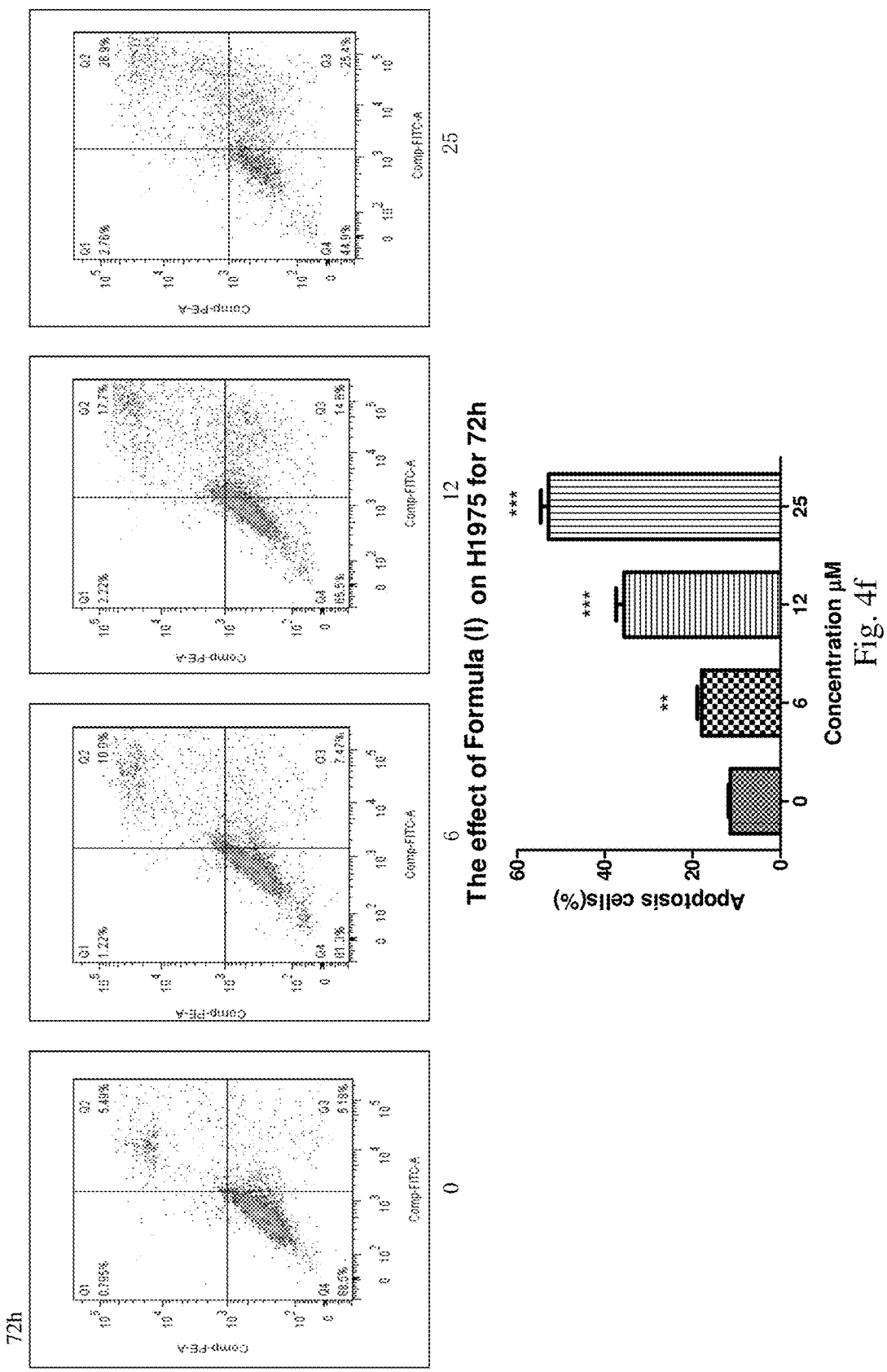

PKM2 enzyme activity assay over the concentration of formula I was performed in KINASE GLO® Plus assay. The controls were conducted in the presence of 5% Dimethyl sulfoxide (DMSO) and normalized to 100%±SD. FIG. 2 shows a graph 200 with a X-axis showing concentration and a Y-axis showing PKM2 Enzyme activity. The results in the graph suggest that PKM2 activator formula I could enhance in a dose-dependent manner. (n=3, p<0.005, *p<0.001). The enzyme activity showed the AC50 value of formula I was 5.5±1.0 µM. The maximum PKM2 enzyme activity was more than 200% compared to that in controls.

FIG. 2. shows PKM2 enzyme activity of formula I. The maximal PKM2 activity thereof was more than 200% relative to activity in controls conducted in the presence of 5% DMSO (normalized to 100%±SD)

3. Cytotoxicity Effect of Formula I on NSCLC Cells.

Seven lung cancer cell lines (A549, H1975, HCC827, H820, H1650, H358 and H460) and two normal cell lines (CCD19-LU and BEAS2B) were selected to do the cytotoxic test. Different cells were seeded at 3000-5000 cells per well in 96-well plates in 1640 media, and formula I and DMSO (0.1% final concentration) were added 24 hours later. The viability effect thereof was determined by MTT assay after 48 hours and 72 hours respectively. MTT assay showed the inhibition activity of formula I on cell proliferation on different NSCLC cells and normal cells at two time points, 48 hours and 72 hours. As shown in FIG. 3a-FIG. 3i and FIG. 6.

FIG. 3a-FIG. 3i shows viability effect induced by PKM2 activator formula I in different lung cancer (A549, H1975, HCC827, H820, H1650, H358, H1460) and normal cell (CCD19-LU, BEAS2B) cell lines at two time points. Different cells were seeded at 3000-5000 cells per well in 96-well plates in 1640 media, and formula I and DMSO (0.1% final concentration) were added 24 hours later. Viability was determined by MTT assay after 48 hours and 72 hours respectively.

4. Formula I significantly induced apoptosis in A549 and H1975 cells as examined by quantitative AnnexinV/PI flow cytometry analysis.

Using quantitative apoptosis measurement method, flow cytometry analysis showed that formula I induced significant level of apoptosis in a concentration-dependent manner in both A549 and H1975 cell lines. Compared with the control group, formula I showed significant higher level of apoptosis and the apoptosis level increased in time dependent manner. (n=3, p<0.005, *p<0.001) As shown in FIG. 4a, FIG. 4b, FIG. 4c, FIG. 4d, FIG. 4e and FIG. 4f.

5. Formula I LED to a Dose-Dependent Increase in PKM2 Phosphorylation.

Figure 5A:
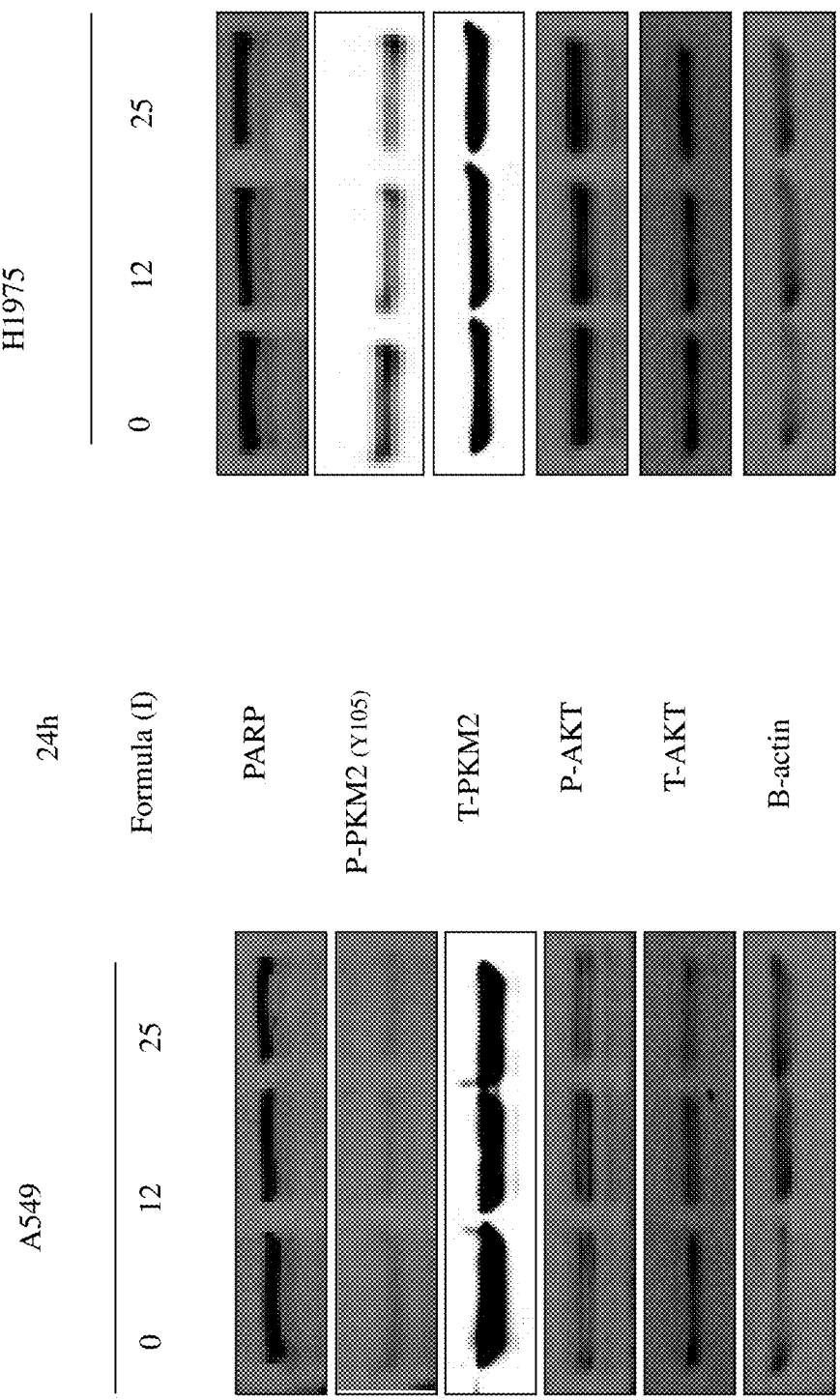
FIG. 5a and FIG. 5b show western-blot result confirmed that PKM2 activator formula I selectively inhibited AKT pathway then induced apoptosis in non-small cell lung cancer (NSCLC) cells A549 and H1975.
Figure 5B:
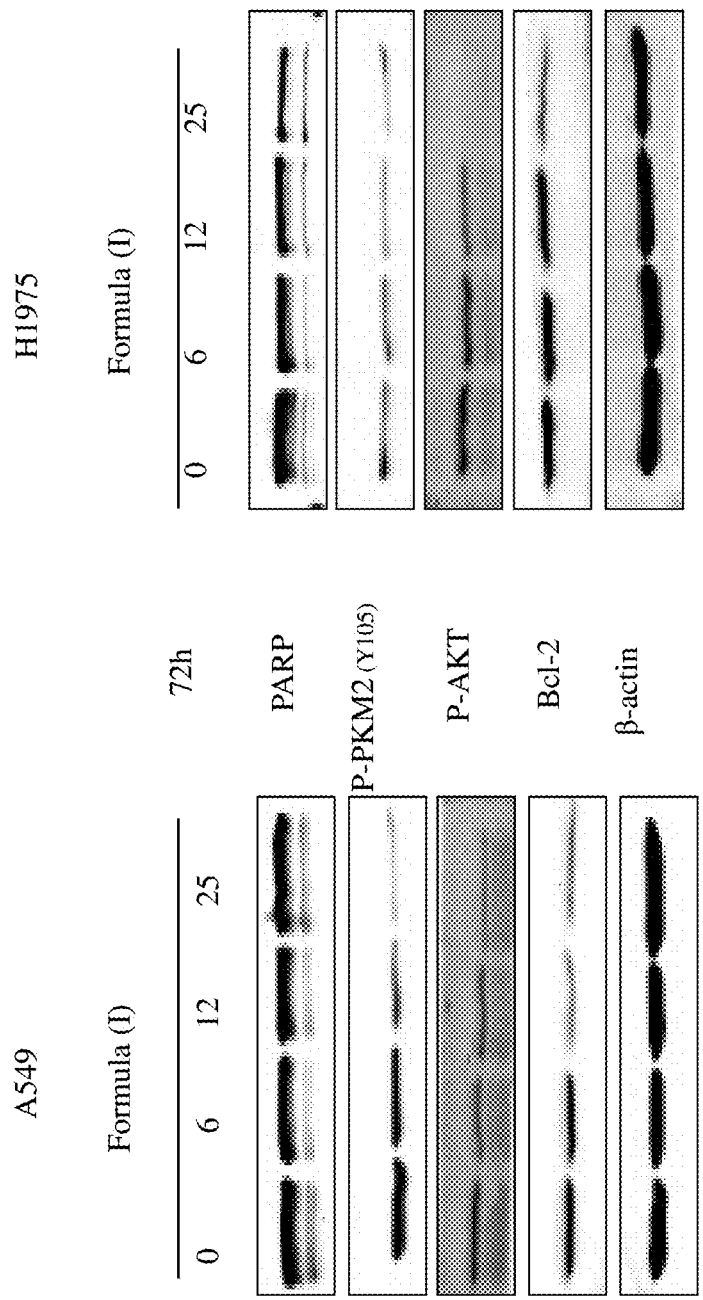

Western blot analysis showed that formula I activated phosphorylation of both PKM2 in a dose-dependent manner in both A549 and H1975 cell lines, indicating the anti-cancer efficacy is mediated by suppression of AKT pathway. And β-actin is used as a loading control and normalization. As shown in FIGS. 5a and 5b.

CONCLUSION

A new PKM2 activator formula I was tested, which targets the last step of glycolysis—PKM2. Results showed its potent anti-cancer activity in NSCLC cells. Formula I exhibited direct PKM2 kinase activation activity, inhibited phosphorylation of AKT and induced apoptosis. As such this formula I can be developed as new anti-cancer drug NSCLC patients by targeting PKM2.

Although the description referred to particular example embodiments, it will be clear to one of ordinary skill in the art that example embodiments in accordance with the invention may be practiced with variation of these specific details. Hence these example embodiments should not be construed as limited to the embodiments set forth herein.

What is claimed is:

1. A method of treating lung cancer in a subject in need thereof, comprising:

administering a therapeutically effective amount of a compound to the subject to treat the lung cancer, wherein the compound is presented by formula I

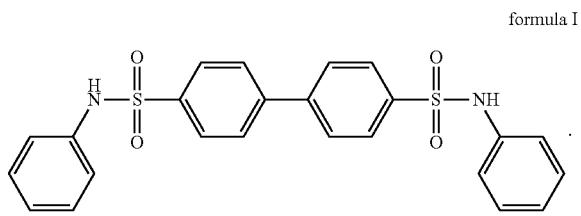 [SMILES: O=S(=O)(Nc1ccccc1)c1ccc(-c2ccc(S(=O)(=O)Nc3ccccc3)cc2)cc1]

formula I

2. The method of claim 1, wherein the lung cancer is Non-Small Cell Lung Cancer.

3. The method of claim 1, wherein the lung cancer is wild type epidermal growth factor receptor (EGFR).

4. The method of claim 1, wherein the lung cancer includes EGFR L858R and T790M mutant.

5. The method of claim 1, wherein the compound activates pyruvate kinase M2 isoform (PKM2) to treat the lung cancer.

6. The method of claim 1, wherein the method further comprises:
   treating the cancer for 48 hours with a concentration of formula I less than 20.22 μM.

7. The method of claim 1, wherein the method further comprises:
   treating the cancer for 72 hours with a concentration of formula I less than 15.40 μM.

8. A method of treating cancer in a subject in need thereof comprising:
   administering a therapeutically effective amount of a compound to the patient to treat the cancer, wherein the cancer includes wild type epidermal growth factor receptor (EGFR), or EGFR L858R and T790M mutant, and the compound is presented by formula I

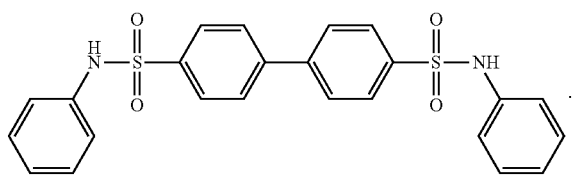

formula I

9. The method of claim 8, wherein the compound activates pyruvate kinase M2 isoform (PKM2) to treat the cancer.

10. The method of claim 8, wherein the cancer is lung cancer.

11. The method of claim 8, wherein the cancer is Non-Small Cell Lung Cancer (NSCLC).

12. The method of claim 8, wherein the method further comprises:
    treating the cancer for 48 hours with a concentration of formula I less than 20.22 μM.

13. The method of claim 8, wherein the method further comprises:
    treating the cancer for 72 hours with a concentration of formula I less than 15.40 μM.

14. A method of treating cancer in a subject in need thereof comprising:
    diagnosing the subject having cancers including wild type epidermal growth factor receptor (EGFR), or EGFR L858R and T790M mutant;
    administering a therapeutically effective amount of a compound to the patient to treat the cancer, and the compound is presented by formula I

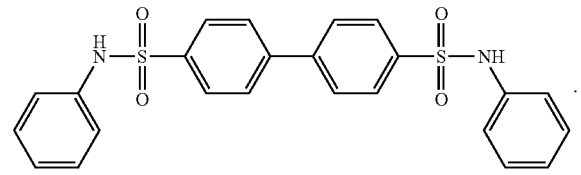

formula I

15. The method of claim 14, wherein the compound activates pyruvate kinase M2 isoform (PKM2) to treat the cancer.

16. The method of claim 14, wherein the cancer is lung cancer.

17. The method of claim 14, wherein the cancer is Non-Small Cell Lung Cancer (NSCLC).

18. The method of claim 14, wherein the method further comprises:
    treating the cancer for 48 hours with a concentration of formula I less than 20.22 μM.

19. The method of claim 14, wherein the method further comprises:
    treating the cancer for 72 hours with a concentration of formula I less than 15.40 μM.

* * * * *